(12) United States Patent
Hyodo et al.

(10) Patent No.: US 11,051,896 B2
(45) Date of Patent: Jul. 6, 2021

(54) MANIPULATOR

(71) Applicant: OLYMPUS CORPORATION, Tokyo (JP)

(72) Inventors: Ryoji Hyodo, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1013 days.

(21) Appl. No.: 15/657,271

(22) Filed: Jul. 24, 2017

(65) Prior Publication Data

US 2017/0325904 A1 Nov. 16, 2017

Related U.S. Application Data

(63) Continuation of application No. PCT/JP2016/051477, filed on Jan. 19, 2016.

(30) Foreign Application Priority Data

Feb. 13, 2015 (JP) .............................. JP2015-026543

(51) Int. Cl.
*A61B 34/30* (2016.01)
*A61B 34/00* (2016.01)
*B25J 18/06* (2006.01)

(52) U.S. Cl.
CPC .............. *A61B 34/73* (2016.02); *A61B 34/30* (2016.02); *B25J 18/06* (2013.01); *A61B 2034/301* (2016.02)

(58) Field of Classification Search
CPC ... A61B 34/30; A61B 34/73; A61B 2034/301; A61B 17/00234; B25J 18/06
See application file for complete search history.

(56) References Cited

U.S. PATENT DOCUMENTS 5,271,543 A * 12/1993 Grant .................. A61B 17/115
227/179.1
5,501,694 A * 3/1996 Ressemann .... A61B 17/320725
604/22
(Continued)

FOREIGN PATENT DOCUMENTS

EP 2409657 A1 1/2012
EP 2 810 607 A1 12/2014
(Continued)

OTHER PUBLICATIONS

Extended Supplementary European Search Report dated Sep. 21, 2018 in European Patent Application No. 16 74 8981.4.
International Search Report dated Mar. 1, 2016 issued in PCT/JP2016/051477.

*Primary Examiner* — William C Joyce
(74) *Attorney, Agent, or Firm* — Scully, Scott, Murphy & Presser, P.C.

(57) ABSTRACT

For bending a manipulator without excessive increase in a tensile force acting on a driving power transmitting member, a manipulator is provided with: an end effector; a driving unit; a guide member to which the end effector is attached at one end thereof and the driving unit is attached at the other end thereof; and a driving power transmitting members that transmit the driving power from the driving unit to the end effector, wherein the guide member includes a guide tube that has lumens, and an outer sheath that has a greater rigidity than the guide tube and that covers an outer circumference of the guide tube, and one end of the outer sheath is movable in a longitudinal direction with respect to the end effector or the driving unit.

9 Claims, 13 Drawing Sheets

(56) References Cited

U.S. PATENT DOCUMENTS

| | | | | |
|---|---|---|---|---|
| 5,643,294 A | * | 7/1997 | Tovey | A61B 17/29 606/148 |
| 6,461,310 B1 | * | 10/2002 | Palmer | A61B 10/06 600/567 |
| 6,689,122 B2 | * | 2/2004 | Yamamoto | A61B 10/06 606/1 |
| 7,329,279 B2 | * | 2/2008 | Haug | A61F 2/2415 623/2.11 |
| 2007/0112355 A1 | | 5/2007 | Salahieh et al. | |
| 2009/0138025 A1 | | 5/2009 | Stahler et al. | |
| 2011/0071564 A1 | | 3/2011 | Suzuki | |
| 2013/0013057 A1 | | 1/2013 | Salahieh et al. | |
| 2013/0289617 A1 | | 10/2013 | Suzuki et al. | |
| 2016/0029875 A1 | | 2/2016 | Okada | |

FOREIGN PATENT DOCUMENTS

| | | |
|---|---|---|
| EP | 3 009 086 A1 | 4/2016 |
| JP | H09-028664 A | 2/1997 |
| JP | 2003-111769 A | 4/2003 |
| JP | 2012-200518 A | 10/2012 |
| JP | 2012-217588 A | 11/2012 |
| JP | 2014-023721 A | 2/2014 |
| JP | 5550150 B2 | 7/2014 |
| WO | WO 2007/058847 A2 | 5/2007 |
| WO | WO 2010/106714 A1 | 9/2010 |
| WO | WO 2013/088840 A1 | 6/2013 |
| WO | 2013/140648 A1 | 9/2013 |
| WO | WO 2014/017124 A1 | 1/2014 |
| WO | 2014/199759 A1 | 12/2014 |

\* cited by examiner

MANIPULATOR

CROSS-REFERENCE TO RELATED APPLICATIONS

This application is a Continuation Application of International Application No. PCT/JP2016/051477 filed on Jan. 19, 2016, which claims priority to Japanese Application No. 2015-026543 filed on Feb. 13, 2015. The contents of International Application No. PCT/JP2016/051477 and Japanese application No. 2015-026543 are hereby incorporated herein by reference in their entirety.

TECHNICAL FIELD

The present invention relates to a manipulator.

BACKGROUND ART

There is a known endoscope, catheter, or manipulator employing a system in which a bending portion or a movable portion (i.e. end effector), such as forceps or the like, disposed at the distal end of an inserted portion is driven by means of wires (for example, see Patent Literatures 1 and 2).

In Patent Literatures 1 and 2, as an elongated flexible inserted portion, an inserted portion in which the outer circumference of a flexible multilumen tube is covered with a coil tube is employed, the wires are made to pass through and are guided in lumens formed in the multilumen tube, and torque transmission is made possible by means of the coil tube.

CITATION LIST

{Patent Literature}
 {PTL 1} Japanese Unexamined Patent Application, Publication No. 2014-23721
 {PTL 2} Publication of Japanese Patent No. 5550150

SUMMARY OF INVENTION

An aspect of the present invention is a manipulator including: an end effector; a driving unit that generates a driving power to be supplied to the end effector; a wire that transmits the driving power from the driving unit to the end effector; and a flexible elongated guide member to which the end effector is attached at one end thereof and the driving unit is attached at the other end thereof, the flexible elongated guide member including: an elongated guide tube that has a lumen through which the wire passes in a longitudinal direction; an outer sheath that has a greater rigidity than the elongated guide tube and that covers an outer circumference surface of the elongated guide tube; and a lock mechanism that immobilizes the outer sheath at an arbitrary position relative to the driving unit, wherein one end of the outer sheath is attached to the driving unit so as to be movable in the longitudinal direction of the guide tube with respect to the driving unit.

DESCRIPTION OF EMBODIMENT

A manipulator 3 according to an embodiment of the present invention will be described below with reference to the drawings.

Figure 1:
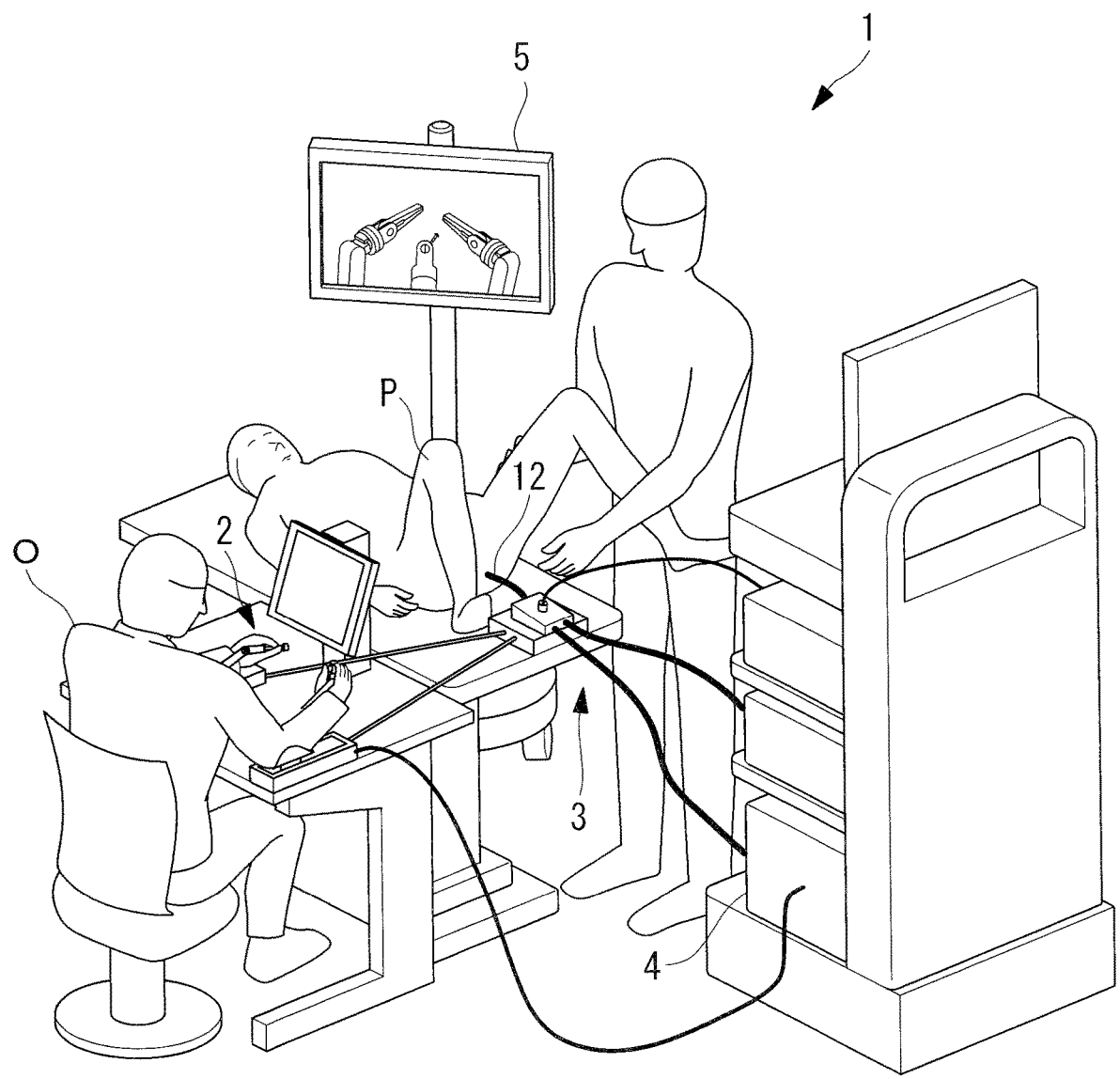
FIG. 1 is an overall configuration diagram showing a medical manipulator system provided with a manipulator according to an embodiment of the present invention.

The manipulator 3 according to this embodiment is employed in, for example, a medical manipulator system 1 shown in FIG. 1. This medical manipulator system 1 is provided with: a master apparatus 2 that is manipulated by an operator O; the manipulator 3 that is inserted into a body cavity of a patient P; a controller 4 that controls the manipulator on the basis of manipulation input to the master apparatus 2; and a monitor 5.

Figure 2A:
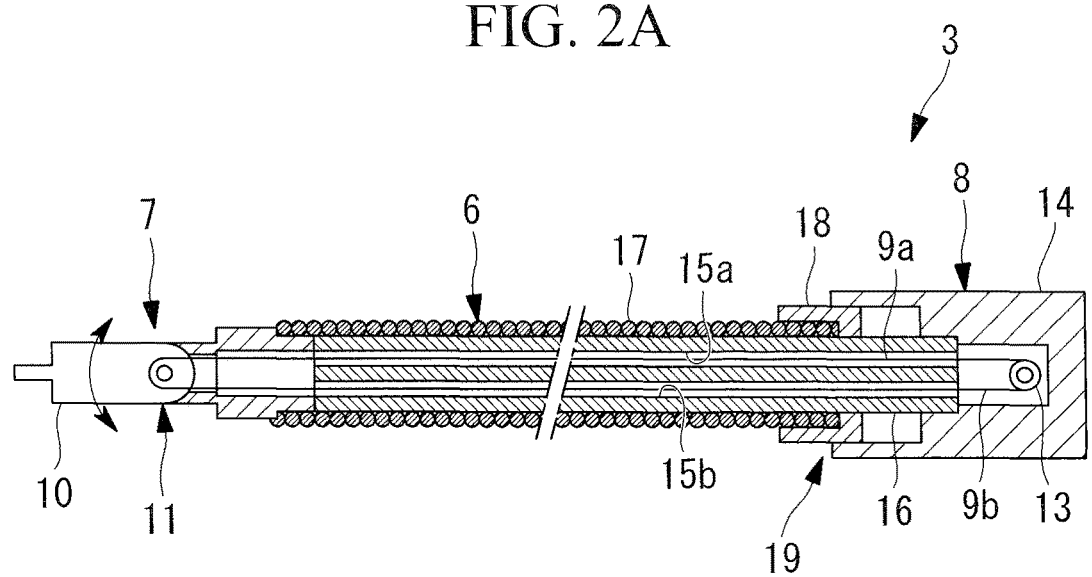
FIG. 2A is a longitudinal cross-sectional view showing a state in which an elongated guide member in the manipulator in FIG. 1 is extended along a straight line.
Figure 2B:
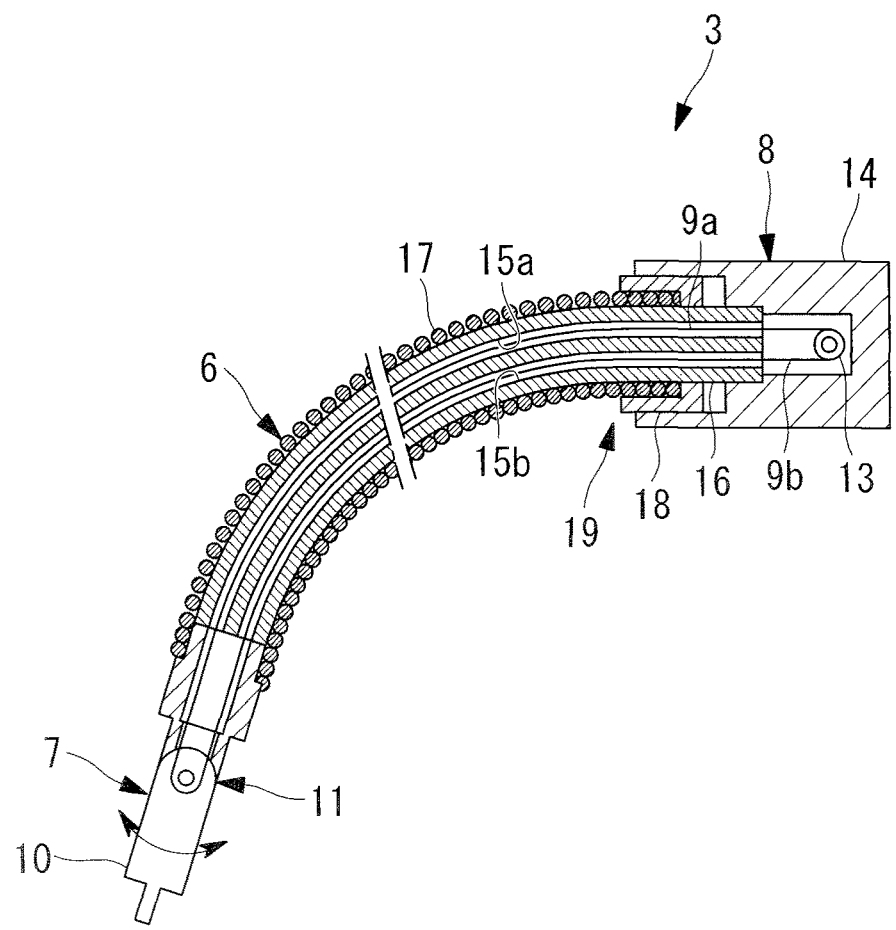
FIG. 2B is a longitudinal cross-sectional view showing a state in which the elongated guide member of the manipulator in FIG. 1 is bent.

As shown in FIGS. 2A and 2B, the manipulator 3 according to this embodiment is provided, for example, with: a flexible elongated guide member 6 that is inserted into the body cavity of the patient P via a channel of an endoscope 12 that is inserted into the body cavity of the patient P; a movable portion 7 that is disposed at a distal end of the elongated guide member 6; a driving unit 8 that is disposed at a proximal end of the elongated guide member 6 and that actuates the movable portion 7 by being controlled by the controller 4; and wires (driving power transmitting members) 9a and 9b that transmit a driving power generated by the driving unit 8 to the movable portion 7.

The movable portion 7 is provided with a treatment unit 10 that acts on an affected area in the body, such as forceps or the like, and at least one articulated portion 11 for supporting the treatment unit 10. In the example shown in the figures, in order to simplify the descriptions thereof, an example of a case in which the articulated portion 11 has a single pivoting joint that pivots the treatment unit 10 about an axis that is orthogonal to the longitudinal axis of the elongated guide member 6 is shown.

The driving unit 8 is provided with a pulley 13 that is connected to a motor (not shown) that generates the driving power, and a housing 14 that supports the pulley 13 so as to be rotatable. The two wires 9a and 9b are wound around the pulley 13, and, when the pulley 13 is rotated by the actuation of the motor, a tensile force acts on one of the wires 9a and 9b wound around the pulley 13 depending on the rotating direction of the pulley 13, and thus, the articulated portion 11 is driven in one direction due to the tensile force transmitted thereto by the wire 9a or 9b.

In this embodiment, the elongated guide member 6 is provided with: a multilumen tube (guide tube) 16 that has two lumens 15a and 15b through which the two wires 9a and 9b pass; a coil tube (outer sheath) 17 that is disposed so as to cover an outer circumference surface of the multilumen tube 16; and a slider 18 that is fixed to a proximal end of the coil tube 17.

The multilumen tube 16 is made of a flexible resin material that has a low rigidity and that is easily deformed. On the other hand, the coil tube 17 is made of a metal material having a greater rigidity than the multilumen tube 16. As shown in FIG. 2A, the coil tube 17 is a tightly wound coil in which strands thereof are tightly touching without gaps when the elongated guide member 6 is in a straight extended state.

The distal end of the multilumen tube 16 is fixed to the articulated portion 11, and the proximal end of the multilumen tube 16 is fixed to the housing 14 of the driving unit 8. In addition, the distal end of the coil tube 17 is also fixed to the articulated portion 11.

The slider 18 is provided so as to be movable in the longitudinal direction of the multilumen tube 16 with respect to the housing 14 of the driving unit 8. By this configuration, the proximal end of the coil tube 17 is supported so as to be movable in the longitudinal direction of the multilumen tube 16. In other words, the housing 14 of the driving unit 8 and the slider 18 constitute a guiding mechanism 19 that supports the proximal end of the coil tube 17 so as to be movable in the longitudinal direction of the multilumen tube 16.

As shown in FIG. 2A, when the elongated guide member 6 is in the straight extended state, a gap is formed between the slider 18 and the housing 14 of the driving unit 8 in the longitudinal direction of the multilumen tube 16.

A case in which treatment is performed inside the body of the patient P by using the thus-configured manipulator 3 according to this embodiment will now be described.

In order to treat an affected area in the body by using the medical manipulator system 1 in FIG. 1, the manipulator 3 according to this embodiment is inserted from the movable portion 7 at the distal end via the channel in the inserted portion of the endoscope 12 that is inserted into the body cavity of the patient P from outside, and the movable portion 7 is made to protrude from an opening of a forceps channel at a distal-end surface of the inserted portion of the endoscope 12 disposed inside the body.

In this case, the body cavity is winding in many cases, and the inserted portion of the endoscope 12 and the channel provided in the inserted portion are inserted into the body cavity by being bent so as to conform to the shape of the body cavity. Therefore, when the manipulator 3 is inserted via such a channel, the manipulator 3 is inserted while bending the elongated guide member 6 in conformity with the channel.

In the manipulator 3 according to this embodiment, when the elongated guide member 6 is bent, the multilumen tube 16 that is disposed along the center thereof and that has a high flexibility is bent. Because the multilumen tube 16 is secured to the movable portion 7 and the driving unit 8 at the two ends thereof, if the multilumen tube 16 is bent without extending/contracting the length thereof along the center line, the lumens 15a and 15b formed in the multilumen tube 16 are also not greatly extended/contracted, and thus, the pathway lengths of the wires 9a and 9b disposed in the lumens 15a and 15b are also not greatly changed.

When the multilumen tube 16 is bent, the coil tube 17 that covers the outer circumference thereof is also bent. Because the coil tube 17 is formed of a material having a sufficiently greater rigidity than the multilumen tube 16, when the elongated guide member 6 is bent, the strands in a portion placed on the radially inner side of the bent portion are kept tightly touching, and thus, the length thereof does not change, whereas a portion placed on the radially outer side of the bent portion is bent so as to increase the intervals between wound portions of the strands.

Figure 3A:
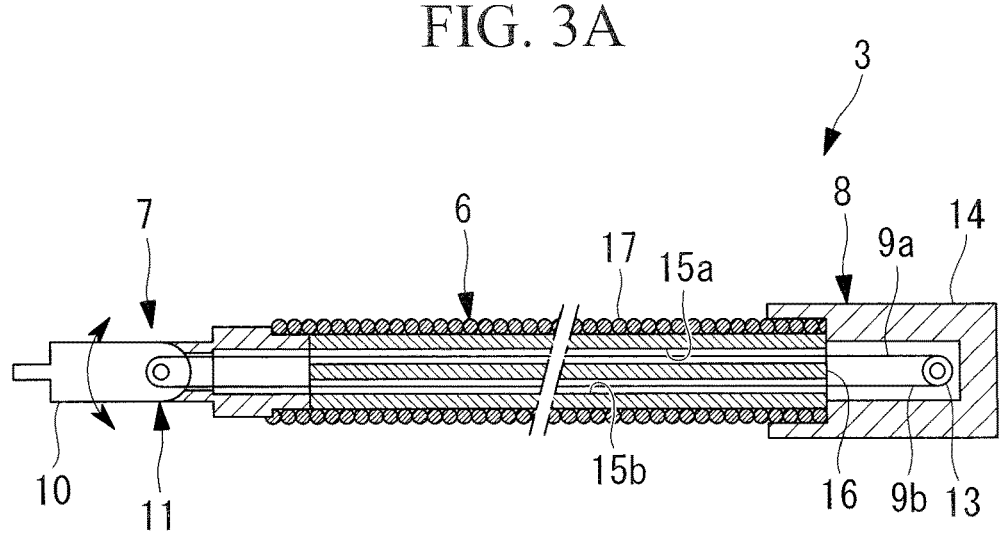
FIG. 3A is a longitudinal cross-sectional view showing, in a straight extended state, a Comparative Example with respect to the manipulator in FIG. 1.
Figure 8:
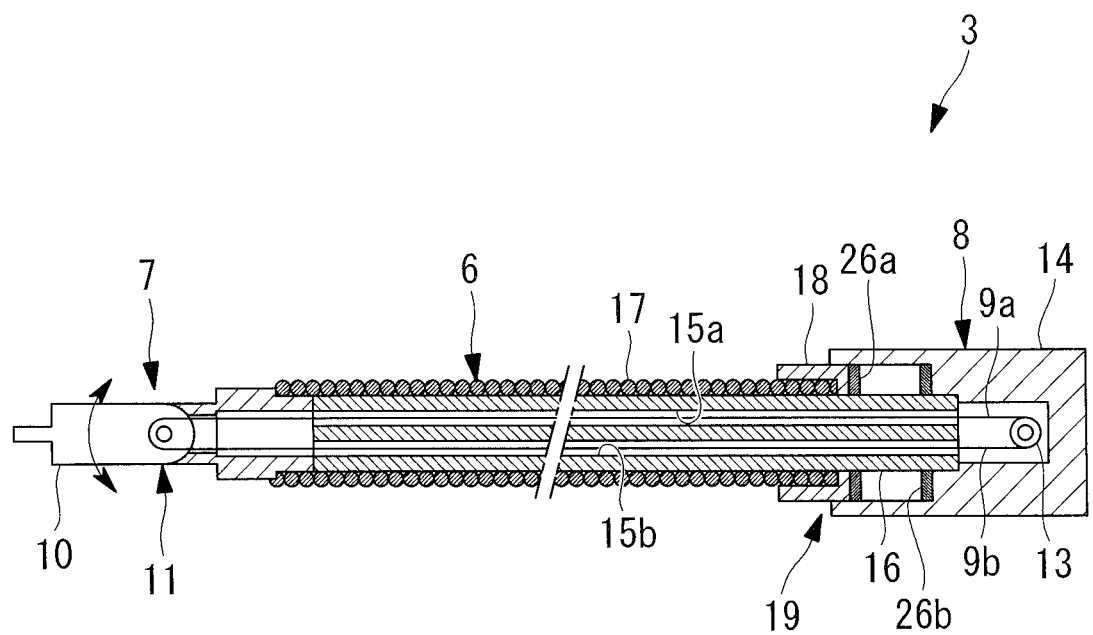
FIG. 8 is a longitudinal cross-sectional view showing a modification of the manipulator in FIG. 1, which is a manipulator provided with a fourth reinforcing unit.

Here, as shown in FIGS. 3A and 8, a Comparative Example will be described in terms of a case in which the two ends of the coil tube 17 are secured to the movable portion 7 and the driving unit 8.

In this case, the dimension of the coil tube 17 on the radially inner side of the bent portion does not change also in the case in which the elongated guide member 6 is in a straight shape and the case in which it is bent. Therefore, when the elongated guide member 6 is bent, the elongated portion is moved or deformed so that the individual members disposed farther outside in the direction of the radius of curvature are stretched relative to the length of the coil tube 17 on the radially inner side of the bent portion.

Figure 3B:
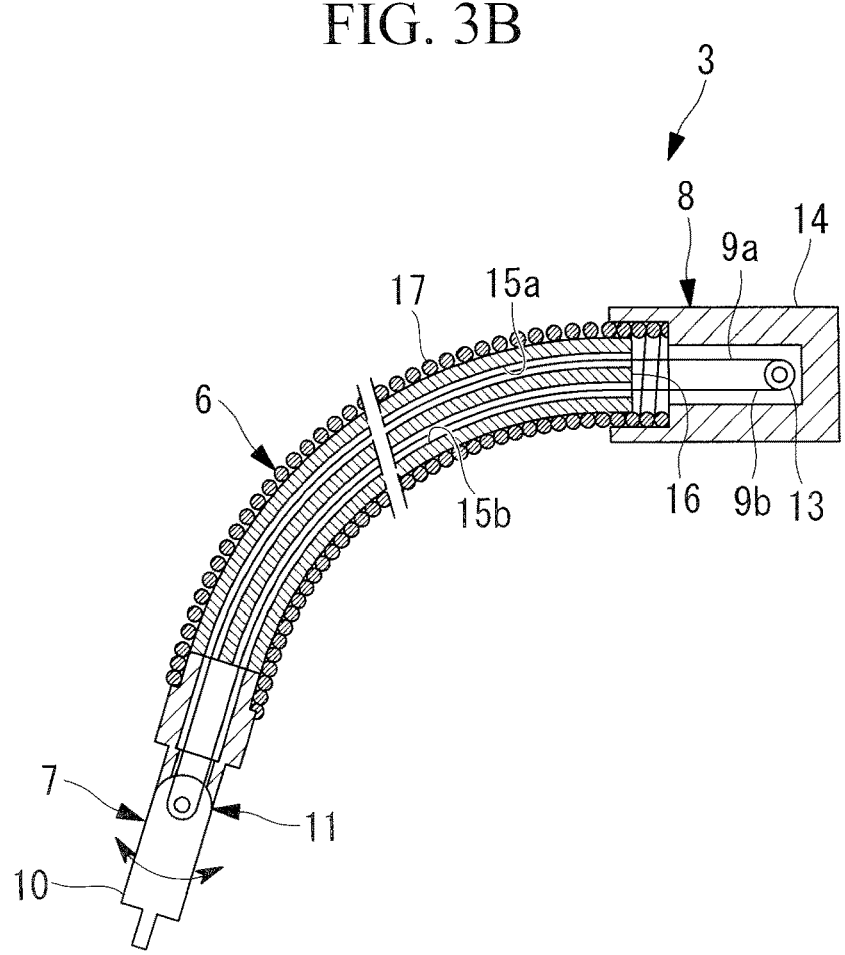
FIG. 3B is a longitudinal cross-sectional view showing, in a bent state, the Comparative Example with respect to the manipulator in FIG. 1.

As a result, as shown in FIG. 3B, because a tensile force acts on the multilumen tube 16 in the direction in which the length thereof is extended, the proximal end thereof is moved in the direction away from the housing 14 of the driving unit 8, and the distance between the movable portion 7 and the driving unit 8 is increased, thus increasing the pathway length of the wire 9a. Because of this, the tensile force applied to the wire 9a, which is disposed so as to pass through the lumen 15a is increased just by bending the elongated guide member 6, and thus, there is a problem in that the movable portion 7 is actuated even though the driving unit 8 is not actuated and that an excessive tensile force is applied to the wire 9a.

In contrast, with the manipulator 3 according to this embodiment, as shown in FIGS. 2A and 2B, because the proximal end of the coil tube 17 is secured to the slider 18 that is movable in the longitudinal direction of the multilumen tube 16 with respect to housing 14 of the driving unit 8, when the elongated guide member 6 is bent, the slider 18 is moved with respect to the housing 14, thus moving the proximal end of the coil tube 17 toward the driving unit 8. In other words, before and after the bending, although there is no difference from the Comparative Example in that the length does not change in the coil tube 17 placed on the radially inner side of the bent portion, because the proximal end of the coil tube 17 is not secured, the proximal end of the coil tube 17 is displaced so as to close the gap between the slider 18 and the housing 14. As a result, an increase in the tensile force in the multilumen tube 16 is prevented, which maintains the length of the multilumen tube 16, and thus, the pathway length of the wire 9a is prevented from being extended.

With such a manipulator 3 according to this embodiment, because the pathway lengths of the wires 9a and 9b do not change even if the elongated guide member 6 is bent, there is an advantage in that it is possible to precisely control the movable portion 7 by preventing the movable portion 7 from being actuated in a manner unrelated to the actuation of the driving unit 8, and by preventing excessive tensile forces from being applied to the wires 9a and 9b.

Note that, in this embodiment, although a multilumen tube formed of a material having a low rigidity is employed as the multilumen tube 16, the rigidity of the elongated guide member 6 itself is increased by the coil tube 17 that covers the outer circumference of the multilumen tube 16. Therefore, the entire manipulator 3 can be moved forward/backward by causing a force along the longitudinal direction to act at the proximal end of the coil tube 17, and the movable portion 7 at the distal end can be rotated about the longitudinal axis by applying a torque about the longitudinal axis at the proximal end of the coil tube 17.

Figure 4:
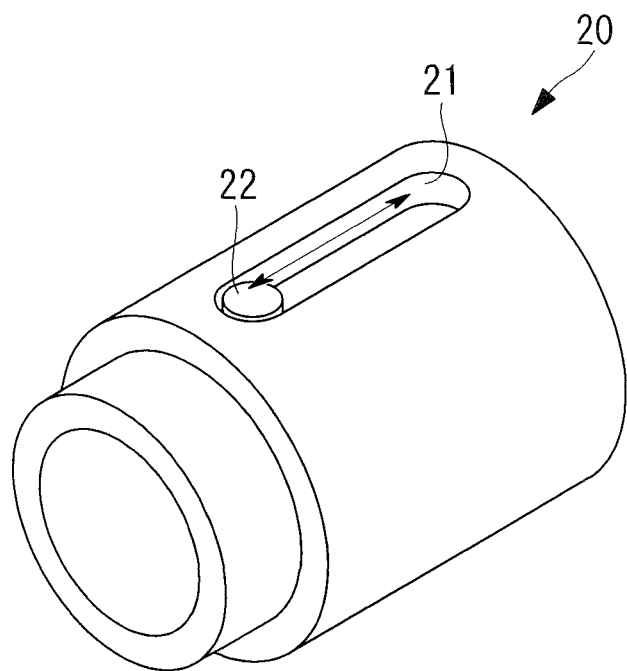
FIG. 4 is a perspective view showing a modification of the manipulator in FIG. 1 and a rotation stopper thereof.

As the method of applying the torque to the coil tube 17, in addition to a method in which the torque is directly applied to the proximal end of the coil tube 17, it is permissible to employ a method in which, as shown in FIG. 4, a rotation stopper 20 that restricts displacements of the slider 18 in the circumferential directions is provided between the housing 14 and the slider 18 that constitute the guiding mechanism 19, and the torque applied to the housing 14 is transmitted to the coil tube 17 via the rotation stopper 20.

As the rotation stopper 20, an elongated hole 21 that extends in the longitudinal direction of the multilumen tube 16 may be provided in the housing 14, and a pin 22 that is inserted into the elongated hole 21 may be provided in the slider 18. When the slider 18 is moved in the longitudinal direction of the multilumen tube 16, it is possible to move the elongated hole 21 with respect to the pin 22, and when a torque is applied to the housing 14, it is possible to transmit the torque about the longitudinal axis of the multilumen tube 16 by means of the engagement between the pin 22 and the elongated hole 21.

In addition, in this embodiment, because the multilumen tube 16 is secured to the housing 14 of the driving unit 8 and the end portion of the coil tube 17 at the proximal end is movable, when the tensile forces are applied to the wires 9a and 9b via the actuation of the driving unit 8, a compressive force is applied to the multilumen tube 16. In the case in which a multilumen tube formed of a material having a low compressive rigidity is employed as the multilumen tube 16, it is preferable that a reinforcing means described below be employed.

Specifically, first, as shown in FIGS. 2A and 2B, the outer surface of the multilumen tube 16 that exhibits a tendency to expand in the radial direction due to compression may be contained by means of the coil tube 17 by keeping the gap in the radial direction between the inner surface of the coil tube 17 and the outer surface of the multilumen tube 16 sufficiently small. In this case, the coil tube 17 also serves as the reinforcing means.

Figure 5:
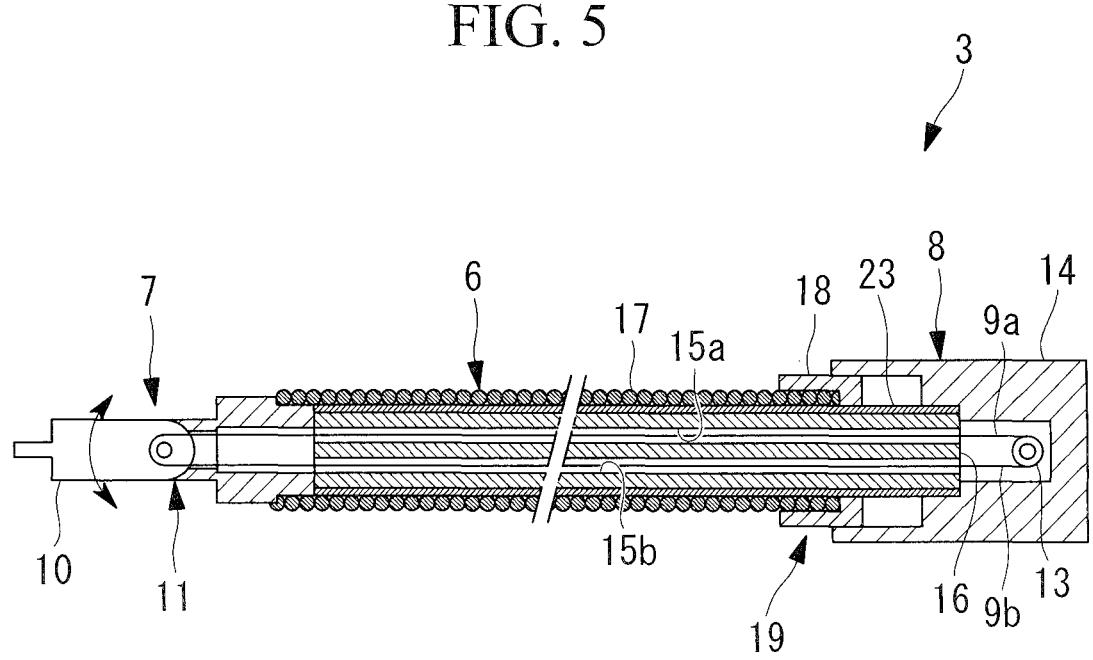
FIG. 5 is a longitudinal cross-sectional view showing a modification of the manipulator in FIG. 1, which is a manipulator provided with and a first reinforcing unit.

Second, as shown in FIG. 5, a resin tube (reinforcing member) 23 that covers the outer circumference surface of the multilumen tube 16 and that has a greater compressive rigidity than the multilumen tube 16 may be employed as the reinforcing means.

Figure 6:
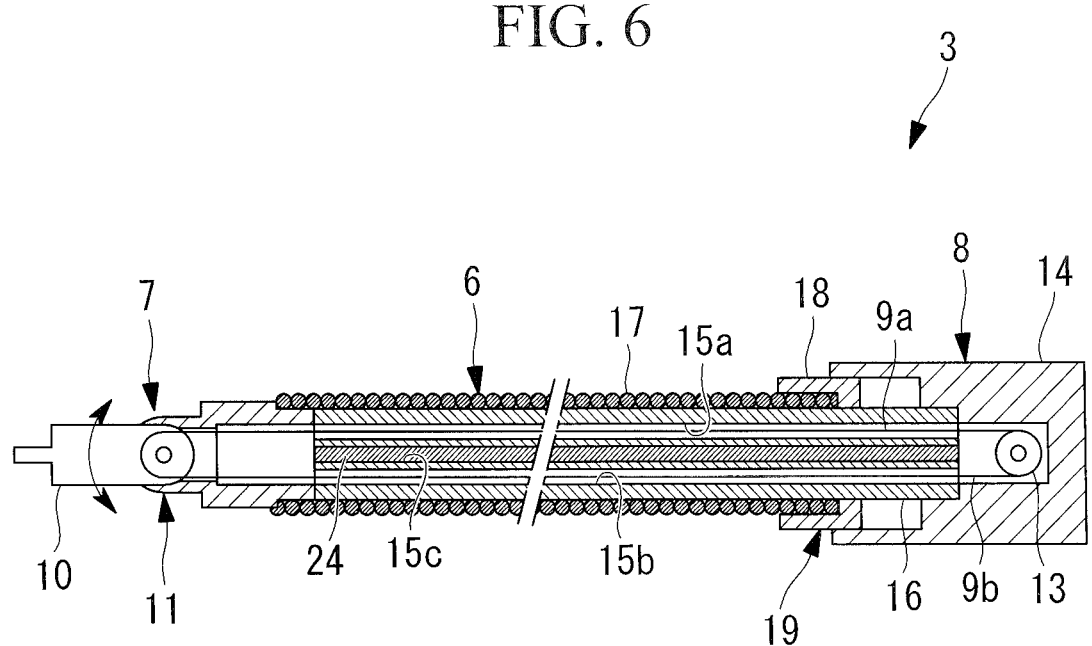
FIG. 6 is a longitudinal cross-sectional view showing a modification of the manipulator in FIG. 1, which is a manipulator provided with a second reinforcing unit.

Third, as shown in FIG. 6, a shaft 24 that is inserted into one of the lumens 15c of the multilumen tube 16 and that has a greater compressive rigidity than the multilumen tube 16 may be employed as the reinforcing means.

Figure 7:
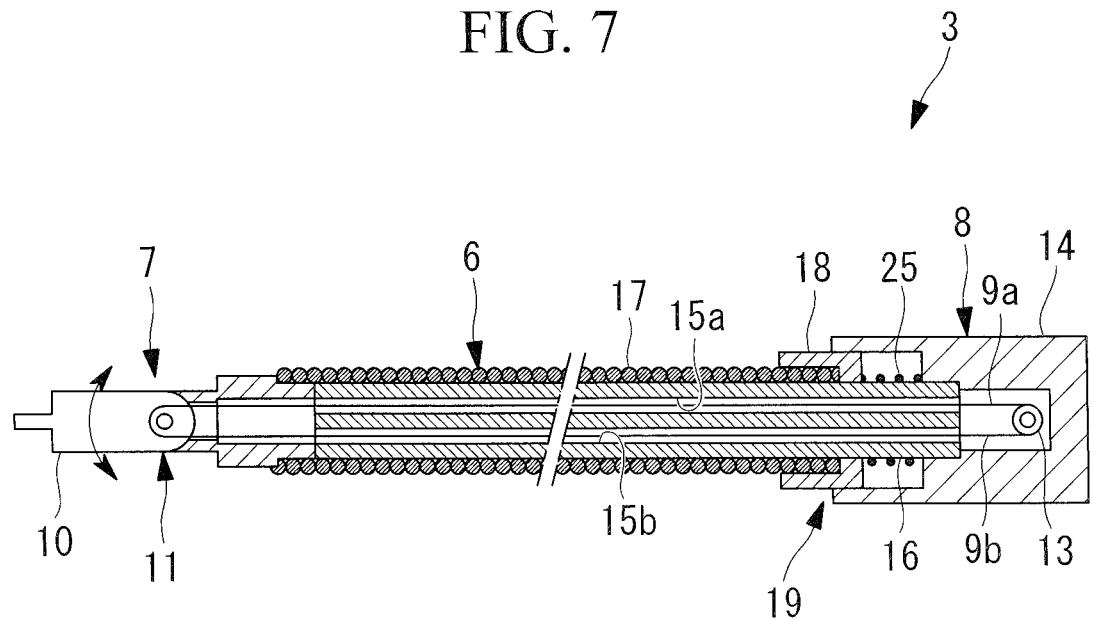
FIG. 7 is a longitudinal cross-sectional view showing a modification of the manipulator in FIG. 1, which is a manipulator provided with a third reinforcing unit.

In addition, fourth, as shown in FIG. 7, a compression spring (biasing means) 25 that is disposed at an interval position between the slider 18 and the housing 14 in the longitudinal direction and that causes a spring force to act in the direction in which the interval is increased may be employed as the reinforcing means. It is possible to reinforce, by means of the spring force of the compression spring 25, the compressive force that is applied to the multilumen tube 16 due to the tensile forces applied to the wires 9a and 9b when actuating the movable portion 7. Note that, in the case in which the compression spring 25 is constituted of a compression coil spring, by employing a coil spring that has an inner diameter that brings the coil spring close to the outer circumference surface of the multilumen tube 16 as with the coil tube 17, it is also possible to suppress an expansion of the multilumen tube 16 in the radial direction due to compression caused by the tensile forces applied to the wires 9a and 9b.

In addition, fifth, as shown in FIG. 8, a pair of magnets (biasing means) 26a and 26b that increase the interval between the slider 18 and the housing 14 in the longitudinal direction by means of magnetic repulsive forces may be employed, in the slider 18 and the housing 14, as the reinforcing means. It is possible to reinforce, by means of the magnetic repulsive forces, the compressive force that is applied to the multilumen tube 16 due to the tensile forces applied to the wires 9a and 9b when actuating the movable portion 7.

In addition, it is permissible to provide a lock mechanism 27 that, by bending the elongated guide member 6, locks relative positions of the slider 18 and the housing 14 in a state in which the slider 18 is moved in the direction in which the slider 18 is brought close to the housing 14. In other words, with the manipulator 3 of this embodiment that is inserted into the channel that is bent by inserting the endoscope 12 into the body cavity, although the elongated guide member 6 is bent in conformity with the shape of the channel, the shape of the elongated guide member 6 does not greatly change after the insertion is completed.

Therefore, by locking the relative positions of the slider 18 and the housing 14 in a state in which the slider 18 is brought close to the housing 14 by actuating the lock mechanism 27, it is possible to receive, by the coil tube 17, the compressive force applied to the multilumen tube 16. In this case, the lock mechanism 27 constitutes the reinforcing means.

As the lock mechanism 27, it is possible to employ a lock mechanism having a structure described below.

Figure 9A:
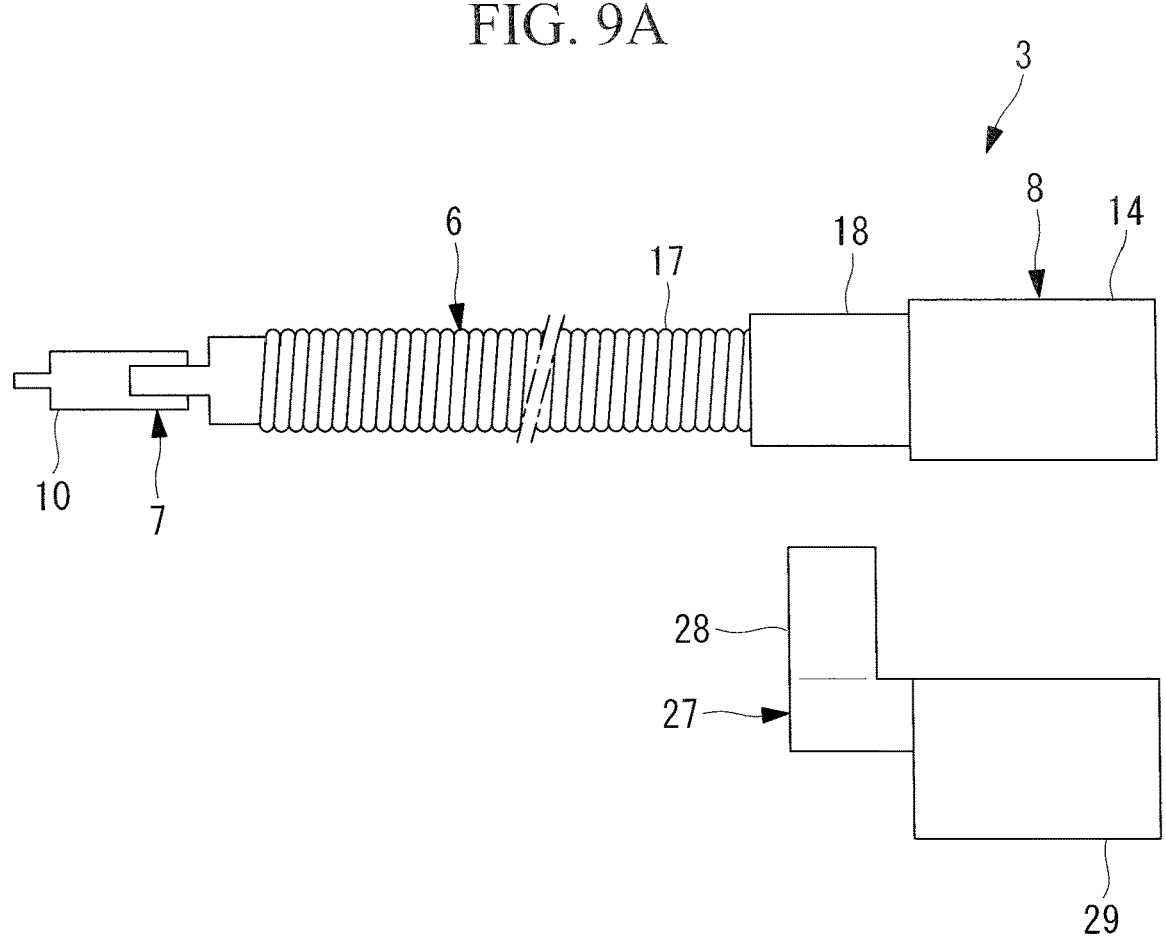
FIG. 9A is a side view showing a modification of the manipulator in FIG. 1, which is a manipulator provided with a lock mechanism, the diagram showing an unlocked state.
Figure 10A:
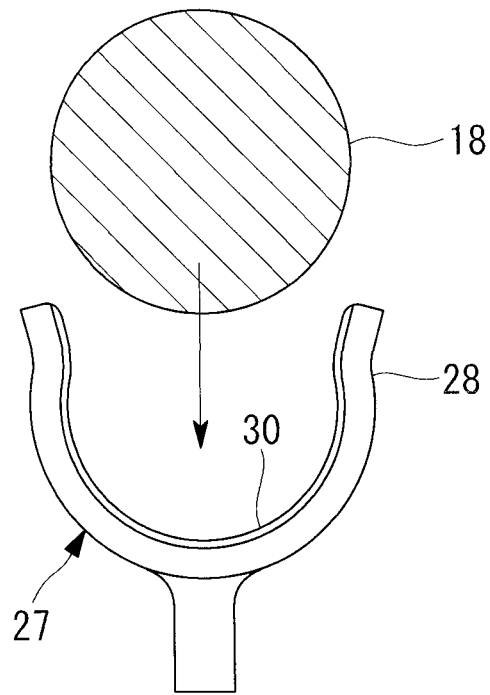
FIG. 10A is a front view showing the unlocked state for explaining the lock mechanism in FIG. 9.

For example, as the lock mechanism 27, as shown in FIGS. 9A and 10A, it is permissible to employ a gripping member 28 that is brought close to the cylindrical slider 18 from the radially outer side thereof and that has a substantially C-shaped cross-sectional shape that accommodates the slider 18 so as to cover the outer circumference surface of the slider 18 substantially half way therearound.

Figure 9B:
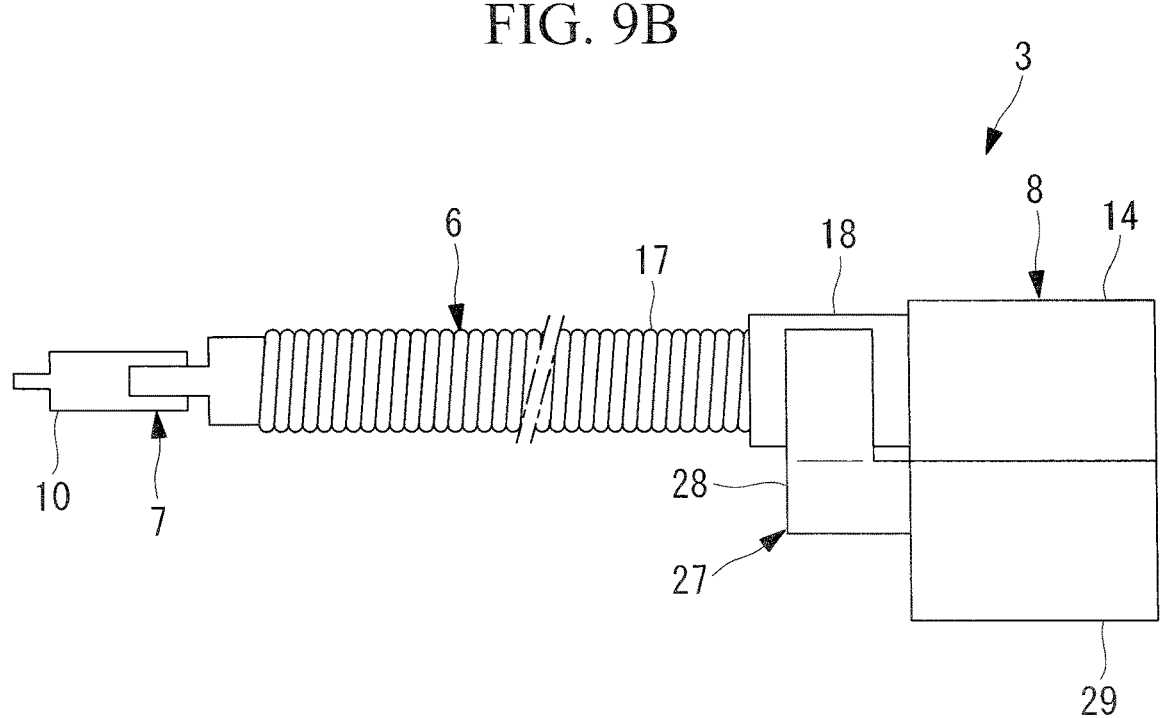
FIG. 9B is a side view showing the modification of the manipulator in FIG. 1, which is the manipulator provided with the lock mechanism, the diagram showing a locked state.
Figure 10B:
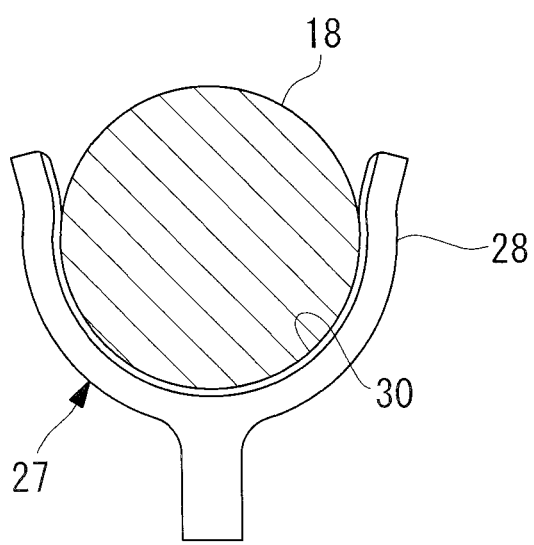
FIG. 10B is a front view showing the locked state for explaining the lock mechanism in FIG. 9.

As shown in FIGS. 9B and 10B, it is permissible to employ a lock mechanism having a structure in which, by forming a motor unit 29 that supplies a driving power to the driving unit 8 as a separate unit from the driving unit 8 in an attachable/detachable manner and by securing the gripping member 28 to the motor unit 29, the gripping member 28 is made to grip the slider 18 when attaching the driving unit 8 to the motor unit 29, and the movements of the slider 18 along the longitudinal direction of the multilumen tube 16 are restrained by means of a friction between the outer circumference surface of the slider 18 and the inner circumferential surface of the gripping member 28. In the figures, reference sign 30 indicates a coating formed of a material that increases the friction.

Figure 11A:
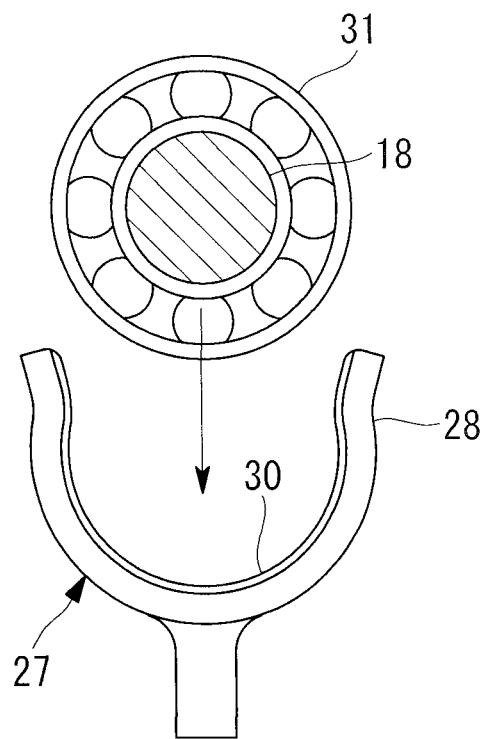
FIG. 11A is a front view showing the unlocked state for explaining another lock mechanism in FIG. 9.
Figure 11B:
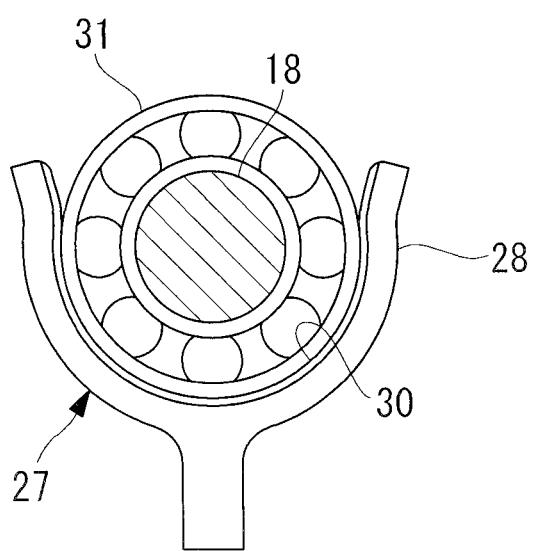
FIG. 11B is a front view showing the locked state for explaining another lock mechanism in FIG. 9.

In addition, as shown in FIGS. 11A and 11B, it is permissible to employ a lock mechanism having a structure in which an outer ring of a bearing 31 secured to the slider 18 is made to engage with the C-shaped gripping member 28 on the inner side thereof, and the movement of the slider 18 along the longitudinal direction of the multilumen tube 16 is prohibited while allowing the slider 18 to be rotated.

Figure 12A:
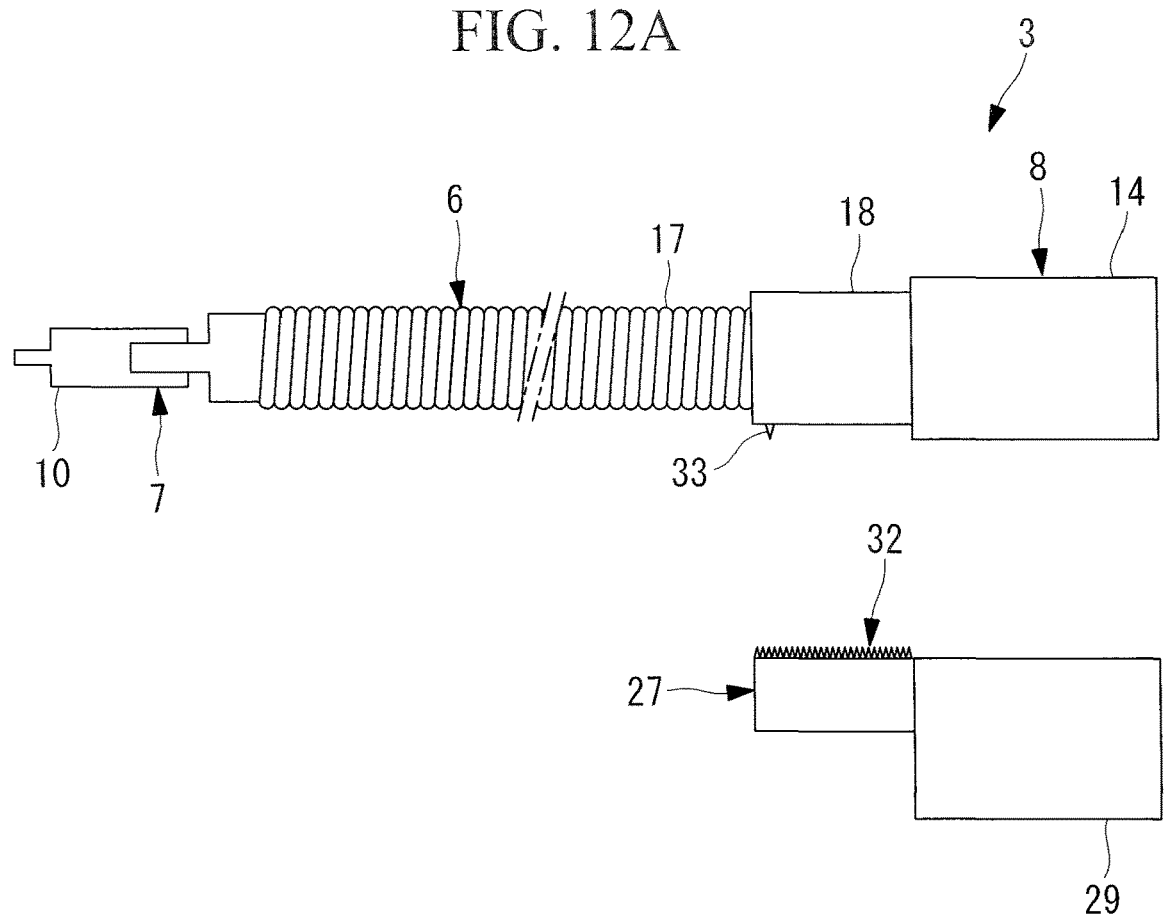
FIG. 12A is a front view showing the unlocked state for explaining another lock mechanism in FIG. 9.
Figure 12B:
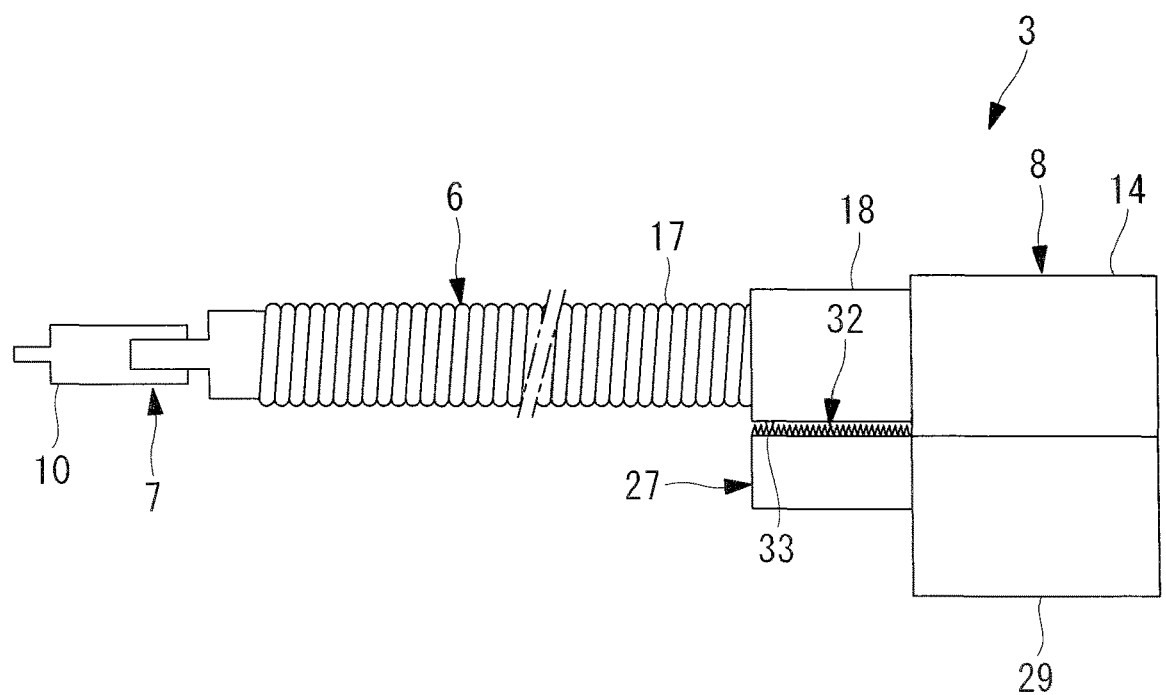
FIG. 12B is a front view showing the locked state for explaining another lock mechanism in FIG. 9.

In addition, as shown in FIGS. 12A and 12B, a plurality of grooves 32 that are arrayed in the direction in which the elongated guide member 6 is disposed may be provided in the motor unit 29, and a protrusion 33 may be provided in the slider 18. It is permissible to employ a lock mechanism having a structure in which the movements of the slider 18 are restrained at an arbitrary position by making the protrusion 33 in the slider 18 engage with one of the grooves 32 when the driving unit 8 is attached to the motor unit 29. The protrusion 33 and the grooves 32 may be switched.

In addition, in this embodiment, although the proximal end of the coil tube 17 is disposed so as to be movable with respect to the driving unit 8, alternatively, the distal end of the coil tube 17 may be disposed so as to be movable with respect to the movable portion 7.

Figure 13A:
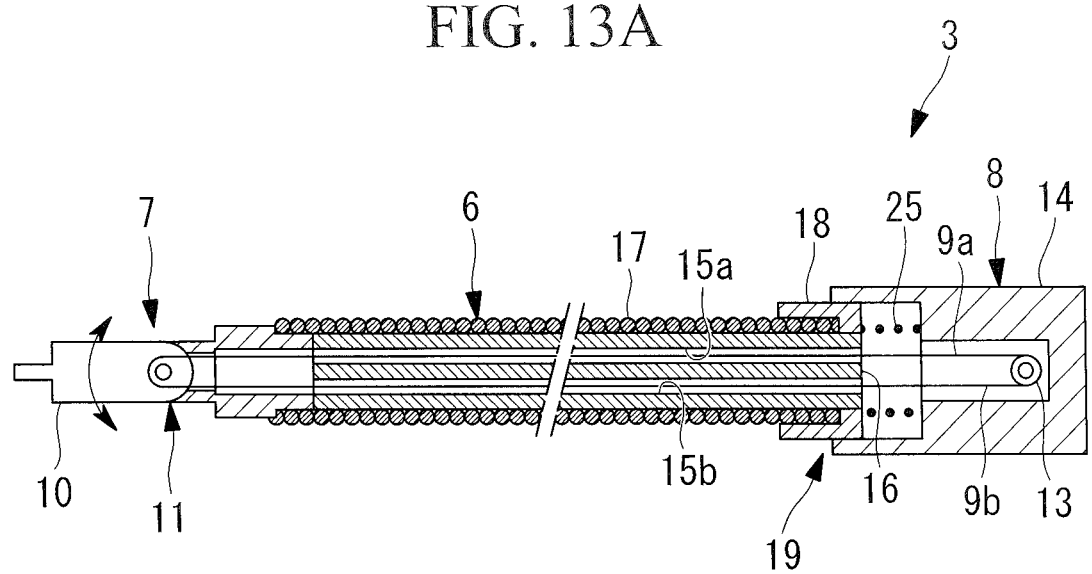
FIG. 13A is a longitudinal cross-sectional view showing, in a straight extended state, another modification of the manipulator in FIG. 1.

In addition, in this embodiment, although the proximal end of the multilumen tube 16 is secured to the housing 14, alternatively, as shown in FIG. 13A, the proximal end of the multilumen tube 16 may be secured to the slider 18, and the compression spring 25 may be disposed between the housing 14 and the slider 18.

Figure 13B:
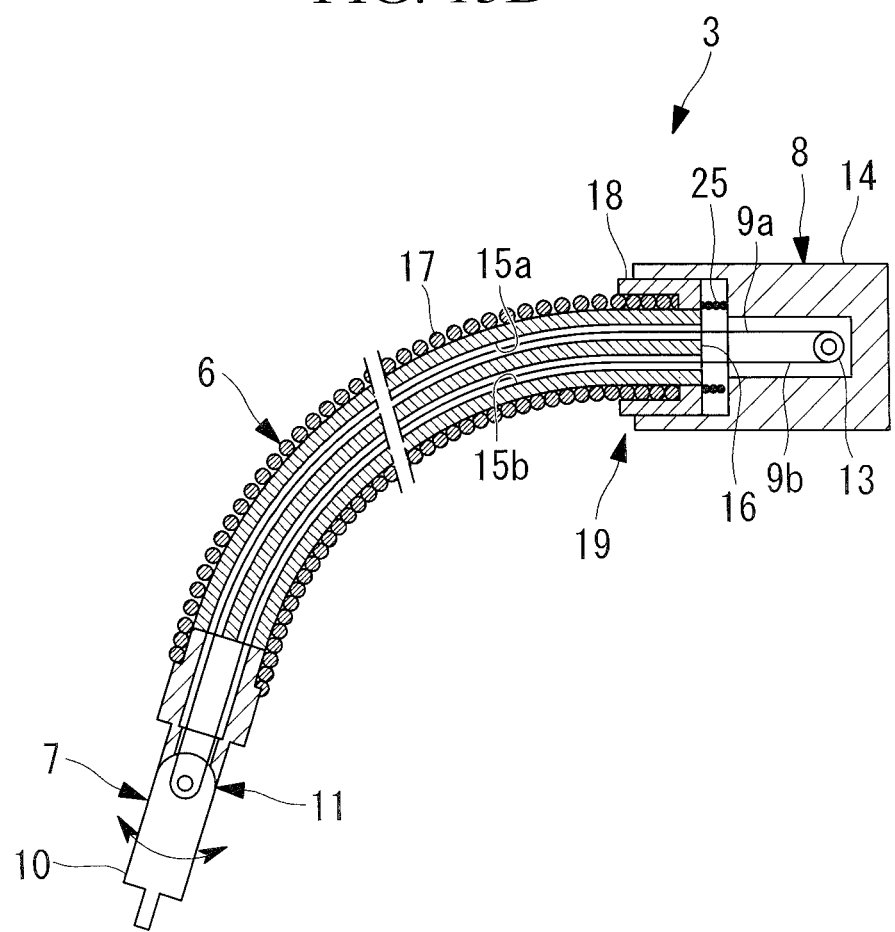
FIG. 13B is a longitudinal cross-sectional view showing, in a bent state, another modification of the manipulator in FIG. 1.

By employing such a configuration, when the elongated guide member 6 is bent, the spring 25 is compressed, thus moving the slider 18, as shown in FIG. 13B. At this time, the proximal end of the multilumen tube 16, which is secured to the slider 18, is also moved due to the movement of the slider 18. Because the multilumen tube 16 is formed of a resin tube having a low rigidity, the multilumen tube 16 is stretched when the proximal end thereof is moved; however, by being moved by an amount corresponding to the amount by which the multilumen tube 16 is stretched, it is possible to prevent an increase in the pathway lengths of the wires 9a and 9b.

Figure 14A:
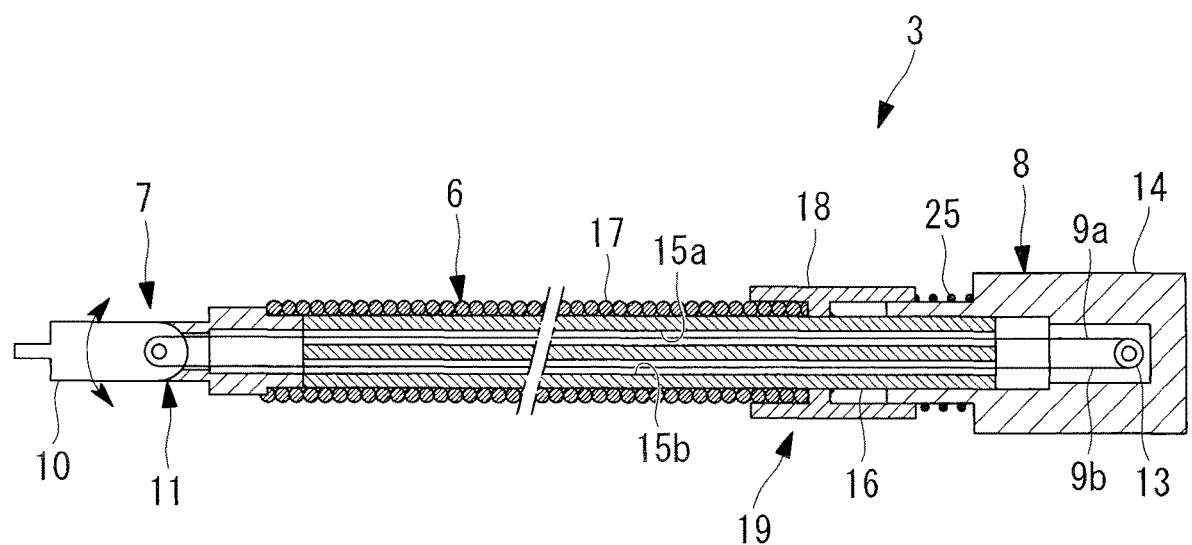
FIG. 14A is a longitudinal cross-sectional view showing, in a straight extended state, another modification of the manipulator in FIG. 1.
Figure 14B:
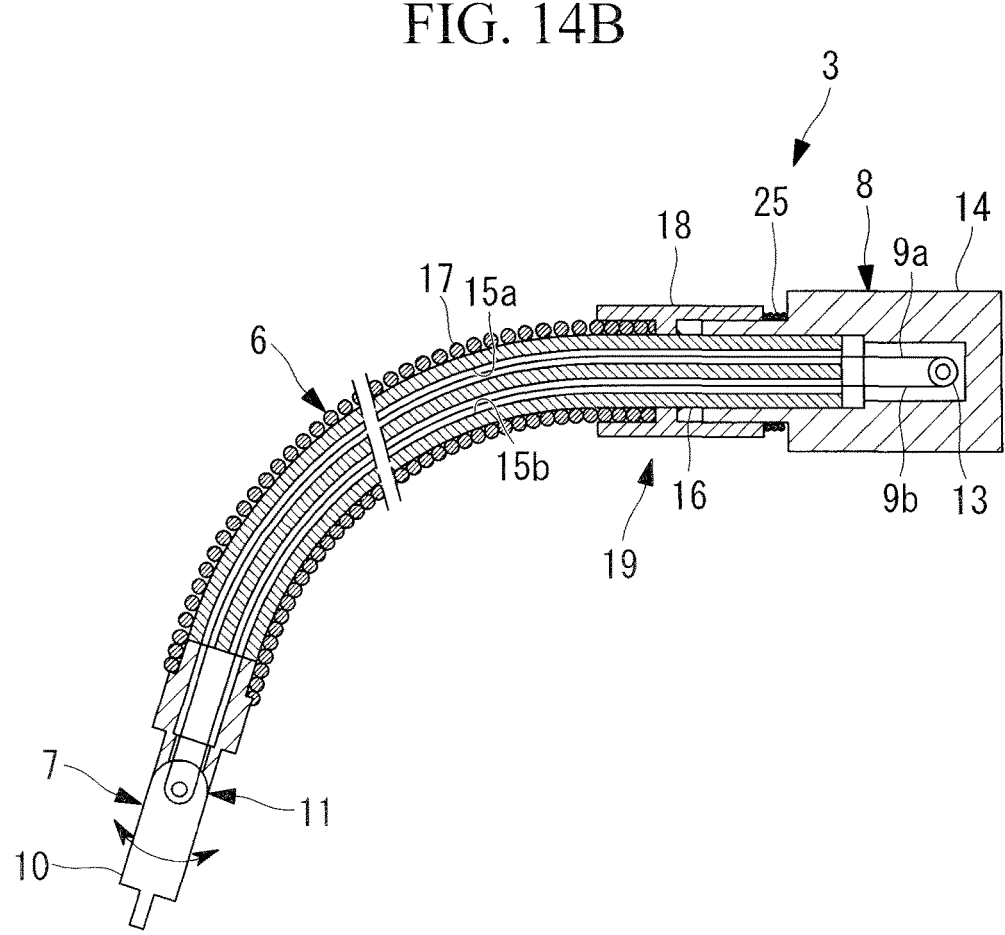
FIG. 14B is a longitudinal cross-sectional view showing, in a bent state, another modification of the manipulator in FIG. 1.

In addition, in this case, as shown in FIGS. 14A and 14B, the multilumen tube 16 may be extended into the housing 14 of the driving unit 8.

Figure 15:
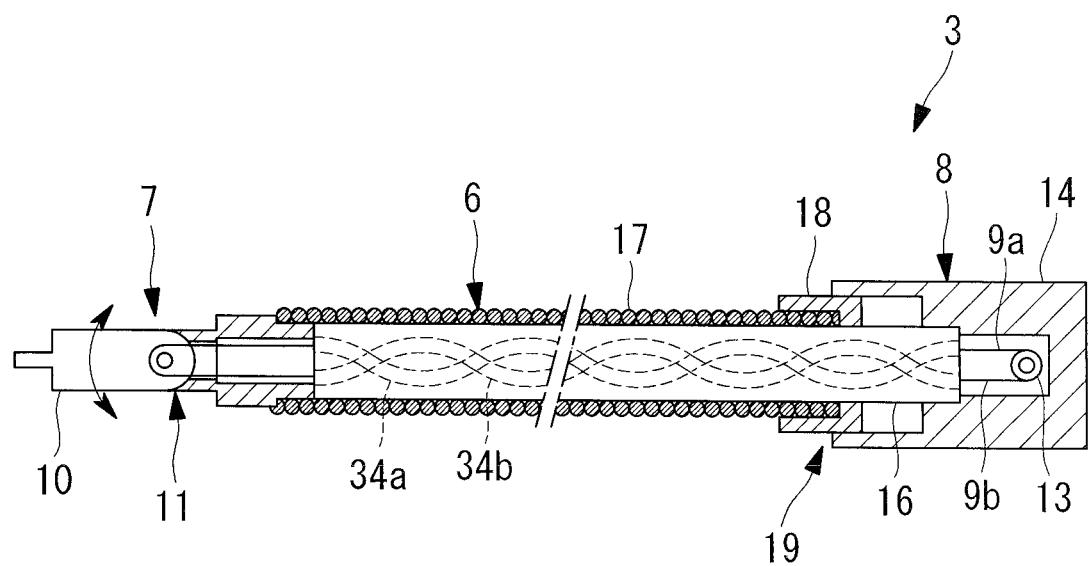
FIG. 15 is a partially cross-sectional longitudinal view showing a modification of the manipulator in FIG. 1, in which, as a guide tube, a multilumen tube having twisted lumens is provided.

In addition, in this embodiment, although the multilumen tube 16 has been described in terms of an example in which the plurality of lumens 15a and 15b are formed straight along the longitudinal direction of the multilumen tube 16, it is not limited thereto, and, as shown in FIG. 15, a multilumen tube 16 having lumens 34a and 34b that are twisted about the longitudinal axis thereof may be employed.

By doing so, by using a multilumen tube 16 having a large diameter, even if a difference in the radius of curvature is increased when being bent, it is possible to prevent changes in the pathway lengths of the wires 9a and 9b by suppressing changes due to bending in the lengths of the individual lumens 34a and 34b.

The inventors have arrived at the following aspects of the invention.

An aspect of the present invention is a manipulator including: a movable portion; a driving unit that generates a driving power to be supplied to the movable portion; a flexible elongated guide member to which the movable portion is attached at one end thereof and the driving unit is attached at the other end thereof; and an elongated driving power transmitting member that transmits the driving power from the driving unit to the movable portion, wherein the elongated guide member includes an elongated flexible guide tube that has a lumen through which the driving power transmitting member passes in a longitudinal direction, and an outer sheath that has a greater rigidity than the guide tube and that covers an outer circumference surface of the guide tube, and at least one end of the outer sheath is attached to the movable portion or the driving unit so as to be movable in the longitudinal direction of the guide tube with respect to the movable portion or the driving unit.

With this aspect, the driving power generated at the driving unit by actuating the driving unit is transmitted to the movable portion via the driving power transmitting member, thus actuating the movable portion. When the elongated guide member is bent, because the guide tube and the outer sheath, which constitute the elongated guide member, are bent, due to which the lumen provided in the guide tube is also bent, and therefore the driving power transmitting member is guided in the bent lumen, transmitting the driving power. In addition, it is possible to transmit, to the movable portion, a torque about a longitudinal axis that is applied at the driving unit by means of the outer sheath having a greater rigidity than the guide tube.

In this case, when the elongated guide member is greatly bent, the length does not change in the high-rigidity outer sheath at a radially innermost portion on the innermost side of the bent portion. Because of this, if two ends of the outer sheath are fixed to the movable portion and a fixed portion, the dimension of the elongated guide member after bending is determined by the radially innermost portion, the guide tube that is disposed on a radially outer side of the bent portion relative to the radially innermost portion is stretched on the basis of the difference in the radius of curvature, and the length of the lumen is also stretched, thus increasing the pathway length of the driving power transmitting member.

With the aforementioned aspect, before and after bending of the elongated guide member, by moving at least one end of the outer sheath in the longitudinal direction of the guide tube with respect to the movable portion or the driving unit, it is possible to compensate the compressed amount of the radially innermost portion by the moved amount of the outer sheath, and thus, it is possible to suppress changes in the pathway length of the driving power transmitting member by suppressing stretching of the guide tube. By doing so, it is possible to bend the elongated guide member while preventing excessive changes in the tensile force in the driving power transmitting member associated with changes in the pathway length.

In the above-described aspect, a guiding mechanism that is provided between the outer sheath and the movable portion or the driving unit and that guides movement of the outer sheath may be provided in the manipulator.

With this configuration, by using the guiding mechanism, the movement of the outer sheath is smoothly guided with respect to the movable portion or the driving unit.

In the above-described aspect, the guiding mechanism may have a rotation stopper that engages the guide tube and the outer sheath in a circumferential direction.

By doing so, by using the guiding mechanism, the outer sheath is guided so as to be movable only in the longitudinal direction of the guide tube with respect to the movable portion or the driving unit, and thus, it is possible to cause a torque to act on the outer sheath via the guiding mechanism.

In the above-described aspect, the outer sheath may be provided with a lock mechanism so as to be movable with respect to the driving unit, and a lock mechanism that immobilizes relative movement between the outer sheath and the driving unit at an arbitrary position.

In this case, the manipulator is inserted into a channel of an endoscope that is bent by being inserted into a body cavity, and the elongated guide member is bent so as to conform to the shape of the endoscope channel. However, the shape of the elongated guide member does not greatly change after the insertion is completed. Because of this, when the elongated guide member is bent, the proximal end of the outer sheath is moved in a direction in which the outer sheath is brought close to the driving unit disposed on the proximal end side. After the insertion of the manipulator into the endoscope channel is completed, by actuating the lock mechanism, relative position of the outer sheath and the driving unit is locked in a state in which the outer sheath is brought close to the driving unit. By doing so, the guide tube is covered with the outer sheath having a greater rigidity over a greater length, and thus, when driving the movable portion by means of the driving unit, it is possible to receive, by the outer sheath, the compressive force applied to the guide tube.

In the above-described aspect, both ends of the guide tube may be fixed to both ends of the outer sheath.

By doing so, when at least one end of the outer sheath is moved with respect to the movable portion or the driving unit, one end of the guide tube is also moved together with the outer sheath. Because changes in the length of the radially innermost portion of the high-rigidity outer sheath due to bending are small, the guide tube that is disposed on the radially outer side of the bent portion is stretched when one end thereof is moved. Because the guide tube is not stretched in a state in which both ends thereof are fixed, but the guide tube is stretched in a state in which at least one end is movable, the pathway length of the driving power transmitting member does not change between the movable portion and the driving unit. With this configuration, it is possible to bend the elongated guide member while preventing excessive changes in the tensile force in the driving power transmitting member associated with changes in the pathway length.

In the above-described aspect, the guide tube may be fixed to the movable portion at one end and thereof fixed to the driving unit at the other end thereof.

By doing so, because the both ends of the guide tube are secured to the movable portion and the driving unit, the pathway length of the driving power transmitting member does not change between the movable portion and the driving unit unless the guide tube is extended/contracted. By making at least one end of the outer sheath movable, it is possible to prevent an action of an external force that causes the guide tube to be extended/contracted by bending.

The above-described aspect may include a reinforcing member for reinforcing a compressive rigidity of the guide tube.

With this configuration, in the case in which the both ends of the guide tube are secured to the movable portion and the driving unit and the outer sheath is moved with respect to the guide tube, there is a portion in which the elongated guide member is formed only of the guide tube. In this case, when actuating the movable portion by means of the actuation of the driving unit, a large compressive force acts on the guide tube due to the tensile force applied to the driving power transmitting member. By reinforcing the guide tube by using the reinforcing member, it is possible to prevent the pathway length of the driving power transmitting member from changing due to the compression of the guide tube.

In the above-described aspect, the outer sheath may be provided so as to be movable with respect to the driving unit, and the reinforcing member may be a biasing member that is disposed between the outer sheath and the driving unit and that generates a force toward a direction with which the outer sheath and the driving unit becomes departed.

With this configuration, when actuating the movable portion by means of the actuation of the driving unit, because it is possible to receive, by the biasing member, the compressive force applied to the guide tube, it is possible to prevent changes in the pathway length due to the compression of the guide tube.

In the above-described aspect, the biasing member may be a compression coil spring.

By doing so, when the elongated guide member is bent, it is possible to allow the movement of the outer sheath with respect to the driving unit by compressing the compression coil spring, and, when the movable portion is actuated by means of the actuation of the driving unit, it is possible to relax the compressive force applied to the guide tube by means of the biasing force of the compression coil spring. In addition, by bringing the inner surface of the compression coil spring close to the outer surface of the guide tube, it is possible to suppress the radially outward expansion of the guide tube, which is subjected to the compressive force, by using the compression coil spring.

In the above-described aspect, the biasing member may be a pair of magnets that are disposed one each in the outer sheath and the driving unit, and that generate magnetic repulsive forces.

With this configuration, when the elongated guide member is bent, it is possible to allow the movement of the outer sheath with respect to the driving unit by resisting the magnetic repulsive forces of the pair of magnets, and, when the movable portion is actuated by means of the actuation of the driving unit, it is possible to relax the compressive force applied to the guide tube by means of the magnetic repulsive forces.

In the above-described aspect, the outer sheath may be provided so as to be movable with respect to the driving unit, and the reinforcing member may be a reinforcing member that has a greater rigidity than the guide tube and that is disposed in a tight-contact state with respect to a surface of the guide tube along a longitudinal direction of the guide tube at least at a space between the outer sheath and the driving unit.

With this configuration, because it is possible to receive, by the reinforcing member, the compressive force applied to the guide tube when the movable portion is actuated by means of the actuation of the driving unit, it is possible to prevent changes in the pathway length due to the compression of the guide tube. The reinforcing member may be a cylindrical member that covers the outer surface of the guide tube or may be a rod-like member that is inserted into the lumen of the guide tube.

In the above-described aspect, the guide tube may have a plurality of lumens, and the individual lumens may have a twisted shape about a longitudinal axis of the guide tube.

With this configuration, when the elongated guide member is bent, even if the guide tube itself has a relatively large outer diameter and the individual lumens are distributed at different positions in the radial directions, changes in the pathway length of a specific lumen due to bending is prevented, and thus, it is possible to prevent the pathway lengths from becoming different among the plurality of lumens.

The aforementioned aspects afford an advantage in which it is possible to bend an inserted portion without an excessive increase in a tensile force that acts on a driving power transmitting member that is made to pass through a lumen.

REFERENCE SIGNS LIST 3 manipulator
6 elongated guide member
7 movable portion (end effector)
8 driving unit
9a, 9b wire (driving power transmitting member)
15a, 15b, 15c, 34a, 34b lumen
16 multilumen tube (guide tube)
17 coil tube (outer sheath)
19 guiding mechanism
20 rotation stopper
23 resin tube (reinforcing member, reinforcing means)
24 shaft (reinforcing means)
25 compression coil spring (compression spring, reinforcing means, biasing means)
26a, 26b magnet (reinforcing means, biasing means)
27 lock mechanism
28 gripping member (lock mechanism)
32 groove (lock mechanism)
33 protrusion (lock mechanism)

The invention claimed is:

1. A manipulator comprising:
an end effector;
a driving unit that generates a driving power to be supplied to the end effector;
a wire that transmits the driving power from the driving unit to the end effector; and
a flexible elongated guide member which includes:
an elongated flexible guide tube that has a lumen through which the wire passes in a longitudinal direction, the guide tube being fixed to the end effector at one end of the guide tube and is fixed to the driving unit at an other end of the guide tube;
an outer sheath that has a greater rigidity than a rigidity of the guide tube, the outer sheath covering an outer circumferential surface of the guide tube;
a slider attached to an end of the outer sheath for movably supporting the outer sheath in the longitudinal direction relative to the driving unit; and
a reinforcing member for resiliently reinforcing a compressive rigidity of the guide tube, wherein the reinforcing member is a biasing member that is disposed proximally relative to the slider and is configured to apply a force to bias the slider in a direction away from the driving unit.

2. The manipulator according to claim 1, wherein the biasing member is a compression coil spring.

3. The manipulator according to claim 1, wherein the biasing member is a pair of magnets that are respectively disposed in the outer sheath and the driving unit, and that generate a magnetic repulsive force.

4. The manipulator according to claim 1, wherein the reinforcing member has a greater rigidity than the guide tube and that is disposed in a tight-contact state with respect to a surface of the guide tube along a longitudinal direction of the guide tube at least at a space between the outer sheath and the driving unit.

5. The manipulator according to claim 1,
wherein the guide tube has a plurality of lumens, and
the individual lumens have a twisted shape about a longitudinal axis of the guide tube.

6. The manipulator according to claim 1, wherein:
the driving unit comprises a housing;
the guide tube is fixed to the housing at the other end such that the other end does not move relative to the housing; and
the biasing member is disposed between the slider and the housing to apply the force to bias the slider in the direction away from the housing.

7. The manipulator according to claim 6, wherein the housing comprises a guiding portion, the slider being movable within the guiding portion.

8. The manipulator according to claim 7, wherein the guiding portion comprising a rotation stopper that engages the guide tube and the outer sheath in a circumferential direction.

9. The manipulator according to claim 8, further comprising a lock mechanism that immobilizes relative movement between the outer sheath and the driving unit at an arbitrary position.

* * * * *